(12) United States Patent
Niki et al.

(10) Patent No.: US 7,651,487 B2
(45) Date of Patent: Jan. 26, 2010

(54) ABSORBENT ARTICLE

(75) Inventors: Yoshifumi Niki, Tochigi (JP); Takahiro Arimura, Tochigi (JP)

(73) Assignee: Kao Corporation, Tokyo (JP)

( * ) Notice: Subject to any disclaimer, the term of this patent is extended or adjusted under 35 U.S.C. 154(b) by 356 days.

(21) Appl. No.: 10/345,303

(22) Filed: Jan. 16, 2003

(65) Prior Publication Data

US 2003/0158534 A1 Aug. 21, 2003

(30) Foreign Application Priority Data

Jan. 16, 2002 (JP) ............................. 2002-007622
Jan. 16, 2002 (JP) ............................. 2002-007623

(51) Int. Cl.
*A61F 13/15* (2006.01)
*A61F 13/20* (2006.01)

(52) U.S. Cl. .................... 604/385.101; 604/385.01; 604/385.24

(58) Field of Classification Search ............ 604/385.01, 604/346–347, 385.03, 358, 385.14, 396, 604/385.24, 385.27
See application file for complete search history.

(56) References Cited

U.S. PATENT DOCUMENTS

| | | | | |
|---|---|---|---|---|
| 4,044,769 A | * | 8/1977 | Papajohn | 604/396 |
| 4,623,342 A | * | 11/1986 | Ito et al. | 604/385.23 |
| 4,678,465 A | * | 7/1987 | Avejic | 604/397 |
| 4,822,435 A | * | 4/1989 | Igaue et al. | 156/164 |
| 5,380,310 A | * | 1/1995 | Mitrani | 604/385.201 |
| 5,558,659 A | | 9/1996 | Sherrod et al. | |
| 5,558,663 A | * | 9/1996 | Weinberger et al. | 604/387 |
| 5,752,946 A | * | 5/1998 | Boberg et al. | 604/385.24 |
| 5,921,975 A | * | 7/1999 | Suzuki et al. | 604/385.17 |
| 6,413,249 B1 | * | 7/2002 | Turi et al. | 604/387 |
| 6,652,499 B1 | * | 11/2003 | Edgren et al. | 604/385.01 |

FOREIGN PATENT DOCUMENTS

| | | |
|---|---|---|
| EP | 1068847 A1 | 1/2001 |
| GB | 2182840 A | 5/1987 |
| JP | 2001-104372 A | 4/2001 |
| JP | 2001-137289 A | 5/2001 |
| WO | WO 91/07155 A1 | 5/1991 |
| WO | WO 0013640 A1 * | 3/2000 |
| WO | WO 2004087027 A1 * | 10/2004 |

* cited by examiner

*Primary Examiner*—Michele Kidwell
(74) *Attorney, Agent, or Firm*—Birch, Stewart, Kolasch & Birch, LLP (57) ABSTRACT

An absorbent article 1 comprises a liquid permeable topsheet 2, a liquid impermeable backsheet 3 and a liquid retentive absorbent core 4 interposed between the topsheet 2 and the backsheet 3, a sheet-like member 6, which is provided at a side edge portion 62 thereof with an elastic member 61, and which is fixed to the backsheet 3 side at an edge portion 63 to 65 excluding the side edge portion 62 where the elastic member 61 is disposed, the absorbent article 1 being deformed such that a concavity is formed on the topsheet 2 side, the absorbent article 1 being put on a wearer while maintaining such a deformed configuration by the sheet-like member 6.

3 Claims, 8 Drawing Sheets

ABSORBENT ARTICLE

This application claims the priority of Japanese Patent Application Nos. 2002-7622, filed Jan. 16, 2002, and 2002-7623, filed Jan. 16, 2002, which are incorporated herein by reference.

BACKGROUND OF THE INVENTION

This invention relates to an absorbent article which can easily be deformed into a configuration suited to exhibit absorptive performance and in which the configuration can stably be maintained during wearing.

Recently, there has been practiced, in order to reduce the economic and physical burden, that a urine absorbing pad is used in combination with a disposable diaper, an undergarment or the like. A urine absorbing pad of this type is deformed along the contour of its wearer's body during wearing.

However, such a deformed configuration is not always a configuration suited to exhibit absorptive performance and a desired absorptive performance is occasionally unobtainable. Although an attempt is made for enhancing absorptive performance, etc. by erecting a leak preventive wall or curving the article itself, by the expanding/contracting force of the elastic member, there are instances where the configuration is not maintained stably and a desired absorptive performance is unobtainable.

It is, therefore, an object of the present invention to provide an absorbent article which can easily be deformed into a configuration suited to exhibit absorptive performance and in which the configuration can stably be maintained during wearing.

SUMMARY OF THE INVENTION

The present invention has achieved the above-mentioned object by providing An absorbent article comprising a liquid permeable topsheet, a liquid impermeable backsheet and a liquid retentive absorbent core interposed between the topsheet and the backsheet, a sheet-like member, which is provided at a side edge portion thereof with an elastic member, being fixed to the backsheet side at an edge portion excluding the side edge portion where the elastic member is disposed, the absorbent article being deformed such that a concavity is formed on the topsheet side, the absorbent article being put on a wearer while maintaining such a deformed configuration by the sheet-like member (the first invention used hereinafter refers to this invention).

Also, the present invention has achieved the above-mentioned object by providing an absorbent article comprising a liquid permeable topsheet, a liquid impermeable backsheet and a liquid retentive absorbent core interposed between the topsheet and the backsheet, at least two sheet-like members, which are each provided at a side edge portion thereof with an elastic member, being disposed on the backsheet side, each of the two sheet-like members being disposed as such that the side edge portion side, where the elastic member is disposed, is directed towards a center side of the absorbent article and fixed to the backsheet side at an edge portion excluding the side edge portion where the elastic member is disposed, the absorbent article being deformed such that a concavity is formed on the topsheet side, the absorbent article being put on a wearer while maintaining such a deformed configuration by the two sheet-like members (the second invention used hereinafter refers to this invention).

Also, the present invention has achieved the above-mentioned object by providing an absorbent article comprising a liquid permeable topsheet, a liquid impermeable backsheet and a liquid retentive absorbent core interposed between the topsheet and the backsheet, a sheet-like member, which is provided at a side edge portion thereof with an elastic portion expansible/contractible in the extending direction of said side edge portion, being fixed to said backsheet side at an edge portion excluding the side edge portion where said elastic portion is located, the absorbent article being deformed such that a concavity is formed on the topsheet side, the absorbent article being put on a wearer while maintaining such a deformed configuration by the sheet-like member (the third invention used hereinafter refers to this invention).

The present invention has achieved the above-mentioned object by providing an absorbent article including a main body portion comprising a liquid permeable topsheet, a liquid impermeable backsheet and a liquid retentive absorbent core interposed between the topsheet and the backsheet, at least two belt-like elastic expansible/contractible members being fixed at opposite end portions thereof to the backsheet side of the main body portion, the main body portion being deformed such that a concavity is formed on the backsheet side, the absorbent article being put on a wearer while maintaining such a deformed configuration by the elastic expansible/contractible members (the fourth invention used hereinafter refers to this invention).

DETAILED DESCRIPTION OF THE PREFERRED EMBODIMENTS

The present invention will be more particularly described with reference to the accompanying drawings, in which.

DETAILED DESCRIPTION OF THE PREFERRED EMBODIMENTS

Figure 1:
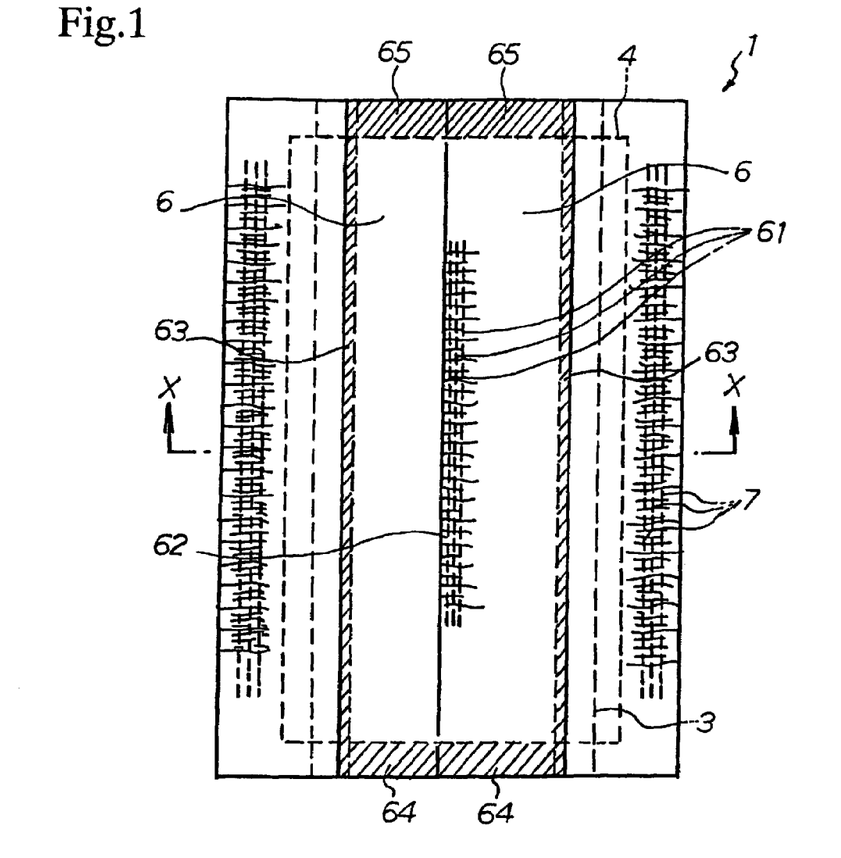
FIG. 1 is a plan view showing a urine absorbing pad according to one embodiment of the present invention (first through third inventions)
Figure 2:
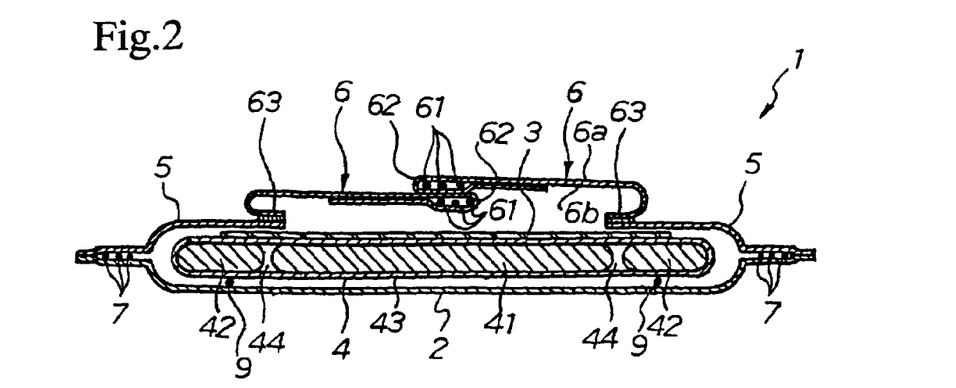
FIG. 2 is a schematic sectional view taken on line X-X of FIG. 1.

The first through third inventions will be described hereinafter based on these preferred embodiments. A urine absorbing pad as one embodiment of the first through third inventions, as shown in FIGS. 1 and 2, comprises a liquid permeable topsheet 2, a liquid impermeable backsheet 3 and a liquid retentive absorbent core 4 interposed between the topsheet 2 and the backsheet 3, and is formed in a substantially vertically elongated configuration. FIG. 1 shows the backsheet 3 side of the urine absorbing pad 1 which is placed in a planarly expanded state.

The urine absorbing pad 1 is of a rectangular configuration, and the topsheet 2 forms its contour. The backsheet 3 is of a rectangular configuration having a width smaller than that of the topsheet 2. The backsheet 3 is disposed at a widthwise central portion of the urine absorbing pad 1 in such a manner as to fully extend between longitudinal opposite end portions thereof.

The absorbent core 4 has a rectangular contour slightly smaller in both length and width than the topsheet 2, and is joined with the topsheet 2 and the backsheet 3 at its portion which is more extended outward than longitudinal opposite end edges of the absorbent core 4. The absorbent core 4 is larger in width than the backsheet 3. That portion of the absorbent core 4 which is more extended outward than the opposite side edges of the backsheet 3 is covered at its one surface side with the topsheet 2 and at its other surface side with a side portion sheet 5. The topsheet 2 and the side portion sheet 5 are joined with each other at those portions which are more extended outward than the longitudinal opposite side edges of the absorbent core 4. A thread-like elastic body 7 for forming side portion gathers is sandwichingly held and fixed between the joined topsheet 2 and side portion sheet 5.

Two sheet-like members 6 each having an elastic member 61 at a side edge portion 62 thereof are fixed to the back sheet 3 side of the urine absorbing pad 1 at edge portions 63 through 65 excluding the side edge portion 62 where the elastic member 61 is disposed.

Specifically, each sheet-like member 6 is in a rectangular configuration having the side edge portion 62 (hereinafter occasionally referred to as the inner edge portion) where the elastic member 61 is disposed, the side edge portion 63 (hereinafter occasionally referred to as the outer side edge portion) opposing the side edge portion 62 and a pair of mutually opposing end edge portions 64, 65.

Each sheet-like member 6 is disposed with its inner edge portion 62 side directed towards a widthwise center side of the urine absorbing pad 1 and is fixed onto the backsheet 3 and/or the side sheet 5 at the edge portion other than the inner edge portion 62, that is, at the outer edge portion 63 and the pair of opposite end edge portions 64, 65, as shown in FIGS. 1 and 2. As means for fixing the edge portion other than the inner edge portion 62, known joining means may be used, such as adhesive agent, heat sealing, ultrasonic sealing and the like. The part not fixed to the sheet-like member 6 can be separated from the top of the backsheet 3.

Figure 3:
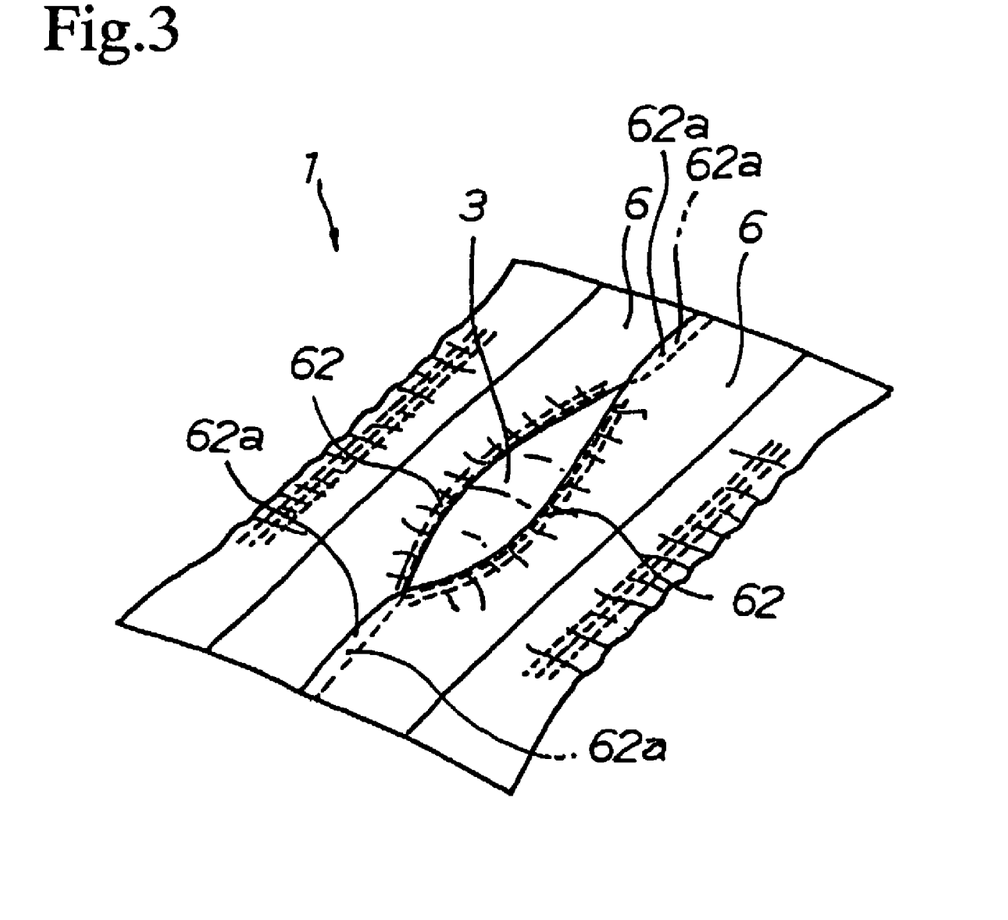
FIG. 3 is a schematic perspective view showing a backsheet side in a natural state of the urine absorbing pad shown in FIG. 1.

The two sheet-like members 6 are, as shown in FIG. 3, overlapped with each other at longitudinal end portions 62a of the side edge portion 62 where the elastic member 61 is disposed.

The urine absorbing pad 1 of this embodiment is deformed such that a concavity is formed on the topsheet 2 side and used while maintaining such a deformed configuration by the sheet-like member 6 which is turned inside out.

Figures 4A, 4B, 4C:
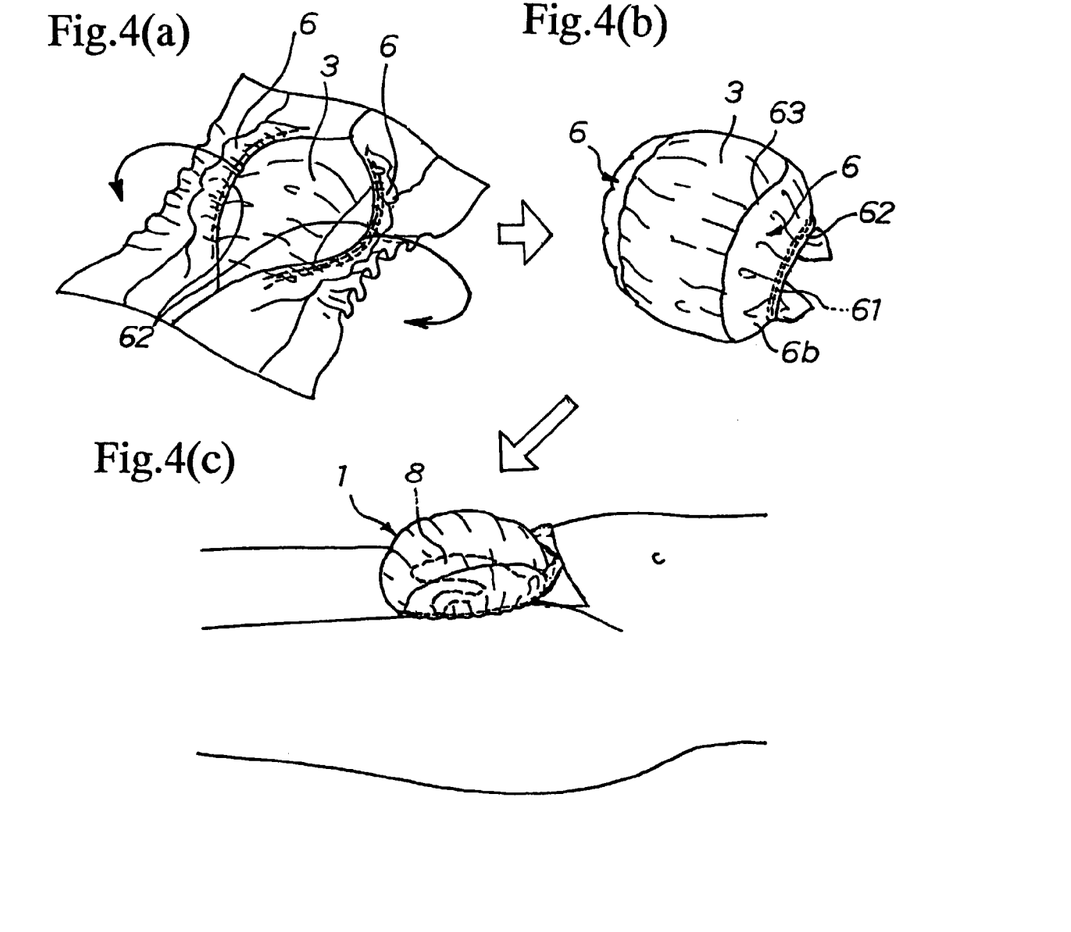
FIG. 4(a), FIG. 4(b), and FIG. 4(c) are explanatory views showing one example of a method for using the urine absorbing pad shown in FIG. 1.

FIGS. 4(a) through 4(c) are explanatory views showing a method for using the present invention as a male urine absorbent pad which is used in such a manner as to surround the male's liquid excretion portion (penis).

First, as shown in FIG. 4(a), the inner edge portions 62 of the two sheet-like members 6 are spread by picking the inner edge portions 62 with the fingers and pulling them leftwards and rightwards. At the same time, the central portion of the urine absorbing pad 1 is pushed from the topsheet 2 side with the finger so that the central portion is pressed into the space between the inner edge portions 62, 62.

As shown in FIG. 4(b), after the topsheet 2 side of the pad 1 is greatly depressed to form a bowl-like configuration, the hand is separated from the sheet-like members 6. Consequently, each sheet-like member 6 is formed in an inverted state where the top surface 6a side and the back surface 6b side are inverted (in a state turned inside out). The deformed configuration is stably maintained by the elastic expanding/contracting force of the elastic member 61 of the sheet-like member 6 and the sheet-like shape of the member 6.

As shown in FIG. 4(c), the deformed pad 1 is put on the male's liquid excretion portion (penis) 8. Such a deformed state is stably maintained during wearing.

Although FIG. 4(b) shows a state in which four corner portions of the pad 1 are exposed from the inside of the concavity formed on the topsheet 2 side of the pad 1, those four corner portions may be received in the concavity.

According to the urine absorbing pad 1 of this embodiment, the pad 1 can easily be deformed into a configuration (for example, a configuration as shown in FIG. 4(b) or FIG. 4(c)) which is suited to exhibit absorptive performance and the configuration is stably maintained during wearing.

Owing to the above features, excellent absorptive performance can be obtained and positional displacement of the pad 1 can be prevented during wearing. In addition, the pad 1 can be put on without manually directly touching the male's liquid excretion portion 8.

Particularly, in this embodiment, since the longitudinal end portions of the inner edge portions 62 of the two sheet-like members 6 are overlapped with each other as shown in FIG. 3, the central portion of the pad 1 pushed between the side edge portions (inner edge portions) 62 where the elastic member is arranged, are pressed by its peripheral entirety. Accordingly, a deeper concavity can be formed. Thus, the pad 1 is further enhanced in shape retainability of the deformed configuration during wearing.

Moreover, the absorbent core 4 in this embodiment comprises, as shown in FIG. 2, a central absorbent core 41, side absorbent cores 42, 42 disposed at opposite sides thereof, and a liquid permeable cover sheet 43 for covering them. Boundary portions between the central absorbent core 41 and the two side absorbent cores 42 each function as a flexible axis 44 for facilitating the easy folding of the absorbent core 4. By providing the flexible axis 44 to the absorbent core 4, the degree of freedom of deformation of the absorbent core is increased and a deeper concavity can be formed on the topsheet 2 side. Thus, wearability for the wearer, absorptive performance, etc. are further enhanced. As shown in FIG. 2, the flexible axis 44 is preferably provided to a part which is overlapped with the outer edge portion 63 of the sheet-like member 6.

As a method for forming a flexible axis on the absorbent core, a method can be employed instead of the method of this embodiment, in which an embossing line is applied to the absorbent core 4, a slit is formed in the absorbent core 4, or other similar arrangement is made with respect to the absorbent core 4. The cover sheet 43 is a liquid permeable sheet made of paper or nonwoven fabric, and it forms the surface of the absorbent core.

The outer edge portions 63 of the sheet-like members 6 in this embodiment are, as shown in FIG. 2, fixed to those parts of the absorbent core 4 which are located widthwise more inside than the opposite side edges of the absorbent core 4. Owing to this arrangement, a part of the absorbent core, which is located more outside than the outer edge portion 63, can be raised together with the sheet-like member 6. Thus, wearability and absorbent performance can be further enhanced.

From a view point to enhance at least one of the features of wearability for the wearer, wearing awareness and absorptive performance, the outer edge portion 63 of each sheet-like member 6 is preferably fixed to the part of the absorbent core 4 which is overlapped with the flexible axis 44. Moreover, the part of the absorbent core 4 which is overlapped with the flexible axis 44 or the those parts of the absorbent core 4 which are overlapped with the opposite side absorbent cores 42 are each preferably provided with an elastic member 9 along the flexible axis 44. Moreover, in FIG. 2, although the elastic member 9 is disposed between the side absorbent core and the topsheet, it may be disposed between the side absorbent core and the backsheet or between the side absorbent core and the side portion sheet.

Figure 5:
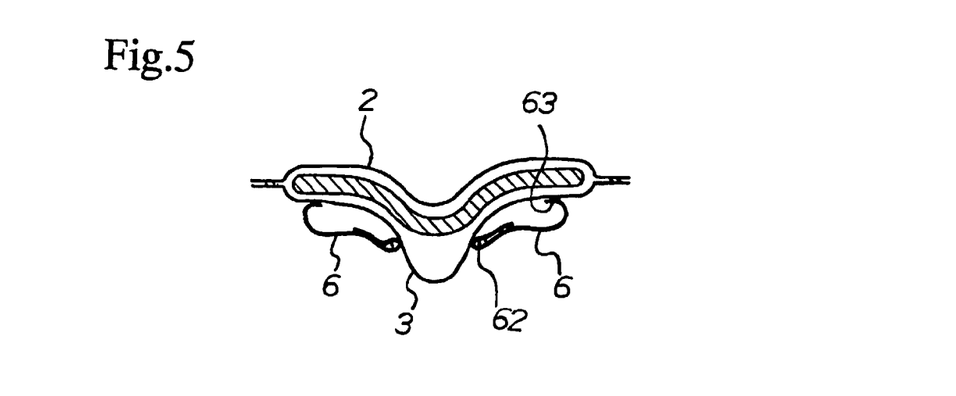
FIG. 5 is a view for explaining another method for using the urine absorbing pad shown in FIG. 1 and is a schematic sectional view showing a widthwise sectional view of the urine absorbing pad in the state shown in FIG. 4(a)
Figure 6A:
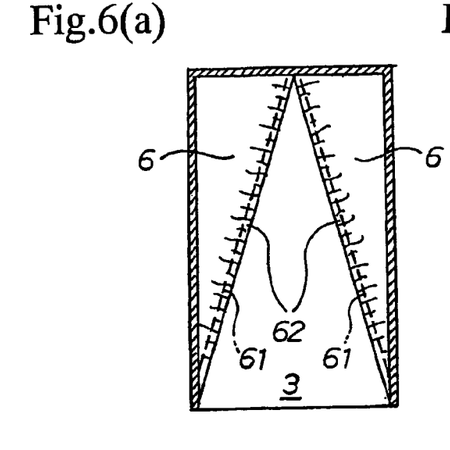
FIG. 6(a), FIG. 6(b), FIG. 6(c), FIG. 6(d) and FIG. 6(e) are schematic plan views showing other embodiments of the present invention.
Figure 6B:
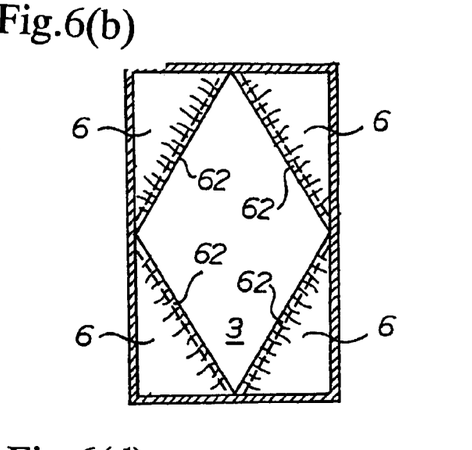
Figure 6C:
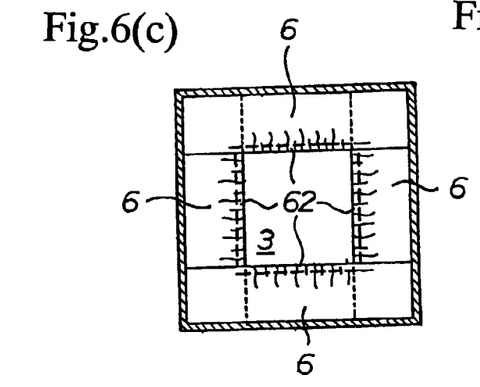
Figure 6D:
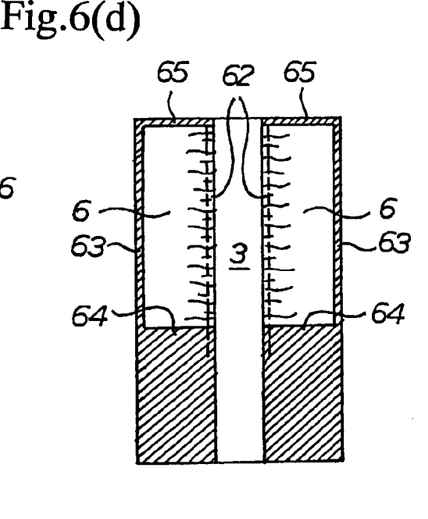
Figure 6E:
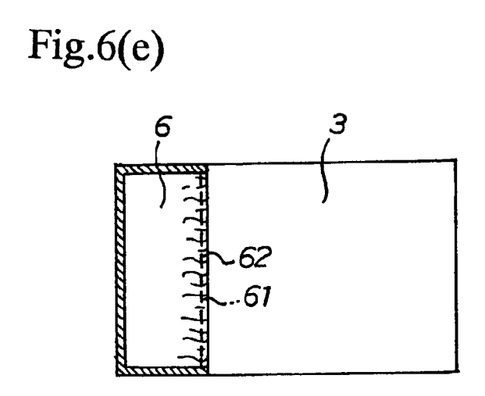

The urine absorbing pad 1 of this embodiment can be used by fixing its configuration by the sheet-like members 6 at the deformed stage shown in FIGS. 4(*a*) and 5. In that case, for example, the concavity on the topsheet 2 side is abutted with the male's or female's liquid excretion portion.

The material for forming the urine absorbing pad 1 of this embodiment will now be described. As for the material for forming the topsheet 2, the backsheet 3 and the absorbent core 4, the material conventionally used for forming an absorbent article of a sanitary napkin, a disposable diaper, etc. can be used without any particular limitation.

As for the material for forming the side sheets 5, a nonwoven fabric, a resin film, a woven fabric, a knitted fabric, a lamination thereof, and the like can be used. Among them, a nonwoven fabric, particularly, a hydrophilic nonwoven fabric is preferable.

As a sheet material for forming the sheet-like member 6, a nonwoven fabric, a resin film, a woven fabric, a knitted fabric, a lamination thereof and the like can be used. Among them, a nonwoven fabric, particularly, a water repellent nonwoven fabric is preferable. As for the material of the elastic member 61 of the sheet-like member 6, a synthetic rubber, a natural rubber, a spandex and the like can be listed. As a form of the elastic member 61, a thread-like form, a belt-like form, a film-like form and the like can be listed. As the elastic members 7 and 9, the same material and form as in the case of the elastic member 61 can be used.

The first through third inventions are not limited to the above-mentioned embodiment. Many changes and modifications can be made without departing from the gist of each invention.

For example, in the above-mentioned embodiment, although plural elastic members 61 are disposed at the inner edge portion 62 of each sheet-like member 6 and an elastic portion, which is expansible and contractible in the extending direction of the side edge portion 62, is formed on the side edge portion 62, in the third invention, an elastic portion, which is expansible and contractible in the extending direction of the side edge portion 62, may be formed on the side edge portion 62 of the sheet-like member 6 by a method other than the method for disposing the elastic members. For example, the entire or a part of the sheet-like member may be formed of an elastic film.

The sheet-like member 6 in the first through third inventions is not limited to a rectangular configuration but it may be in any other desired configuration such as a triangular configuration, a semi-circular configuration, etc. (see FIGS. 6(*a*) and 6(*b*)). The sheet-like members 6 may be disposed and fixed in the manner as shown in FIGS. 6(*a*) through 6(*d*). Moreover, in the first and third inventions, the number of the sheet-like member 6, which is provided at the side edge portion 62 with the elastic member 11 (elastic portion), may be only one (see FIG. 6(*e*)).

Although the sheet-like member 6, which is provided at the side edge portion 62 with the elastic member 11 (elastic portion), may be fixed over the entire area at the edge portion only excluding the side edge portion 62, it may partly have a part which is not fixed.

The absorbent article of the first through third inventions may be a sanitary napkin, a panty liner, a disposable diaper, etc. besides the urine absorbing pad (including an incontinent pad).

The absorbent article of the first through third inventions can easily be deformed into a configuration suited for exhibiting absorptive performance and the configuration is stably maintained during wearing.

The fourth invention will be described hereinafter in detail in the form of its preferred embodiment.

Figure 7:
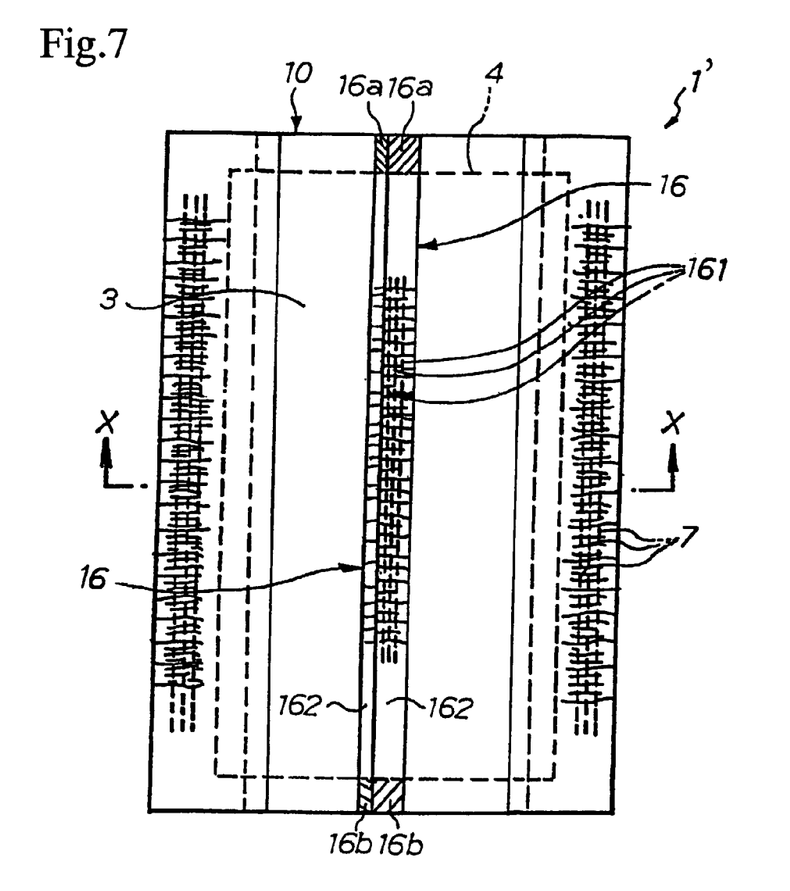
FIG. 7 is a plan view showing a urine absorbing pad according to one embodiment of the present invention (fourth invention)
Figure 8:
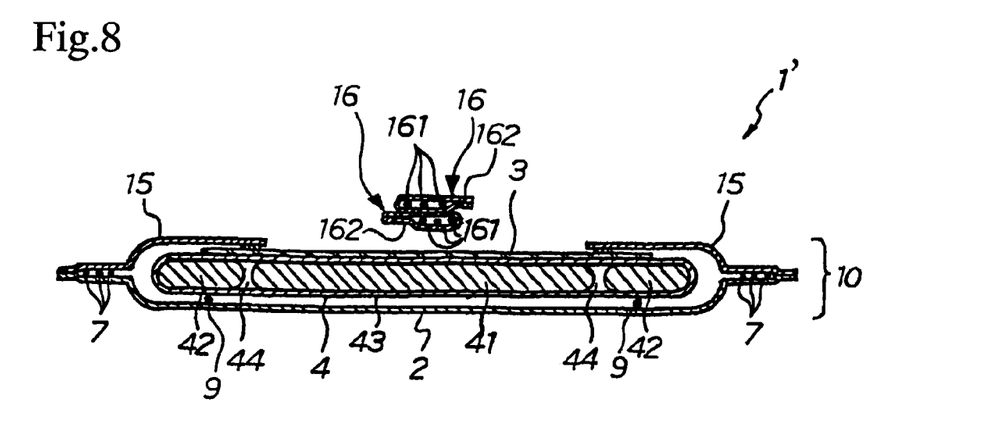
FIG. 8 is a schematic sectional view taken on line X-X of FIG. 7.

A urine absorbing pad 1' as one embodiment of the fourth invention includes a main body portion 10 which comprises, as shown in FIGS. 7 and 8, a liquid permeable topsheet 2, a liquid impermeable backsheet 3 and a liquid retentive absorbent core 4 interposed between the topsheet 2 and the backsheet 3. The main body portion 10 is formed in a substantially vertically elongated configuration. FIG. 7 shows the backsheet 3 side of the urine absorbent pad 1' planarly expanded.

The urine absorbing pad 1' is of a rectangular configuration, and the topsheet 2 forms its contour. The backsheet 3 is of a rectangular configuration having a width smaller than that of the topsheet 2. The backsheet 3 is disposed at a widthwise central portion of the urine absorbing pad 1' in such a manner as to fully extend between longitudinal opposite end portions thereof.

The absorbent core 4 has a rectangular contour slightly smaller in both length and width than the topsheet 2, and is joined with the topsheet 2 and the backsheet 3 at its portion which is more extended outward than longitudinal opposite end edges of the absorbent core 4. The absorbent core 4 is larger in width than the backsheet 3. That portion of the absorbent core 4 which is more extended outward than the opposite side edges of the backsheet 3 is covered at its one surface side with the topsheet 2 and at its other surface side with a second backsheet 15. The topsheet 2 and the second backsheet 15 are joined with each other at those portions which are more extended outward than the longitudinal opposite side edges of the absorbent core 4. A thread-like elastic body 7 for forming side portion gathers is sandwichingly held and fixed between the joined topsheet 2 and side portion sheet 5.

Each elastic expansible/contractible member 16 is formed by fixing a thread-like elastic member 161 in its expanded state between double folded belt-like sheets 162. A plurality of elastic members are spacedly disposed at each elastic expansible/contractible member 16 generally in parallel relation.

The two elastic expansible/contractible members 16 are disposed along the longitudinal direction of the main body portion 10, and their opposite end portions 16a, 16b are fixed to widthwise generally central portions of the main body portion 10, respectively. The opposite end portions 16a, 16b of the elastic expansible/contractible member 16 are preferably fixed to the central portion which occupies ⅓ of the widthwise (left and right direction of FIG. 7) of the main body portion and particularly preferably fixed to the central portion which occupies ⅕ of the afore-mentioned length.

The elastic expansible/contractible members 16 are disposed between the longitudinal opposite end portions of the main body portion 10, and they are fixed onto the backsheet 3 in the portion indicated by phantom lines in FIG. 7. As means for fixing the elastic expansible/contractible members 16 to the main body portion 10, known fixing means such as adhesive agent, heat sealing, ultrasonic sealing and the like can be used. The central portions of the elastic expansible/contractible members 16 are not fixed to the main body portion 10.

Figure 9:
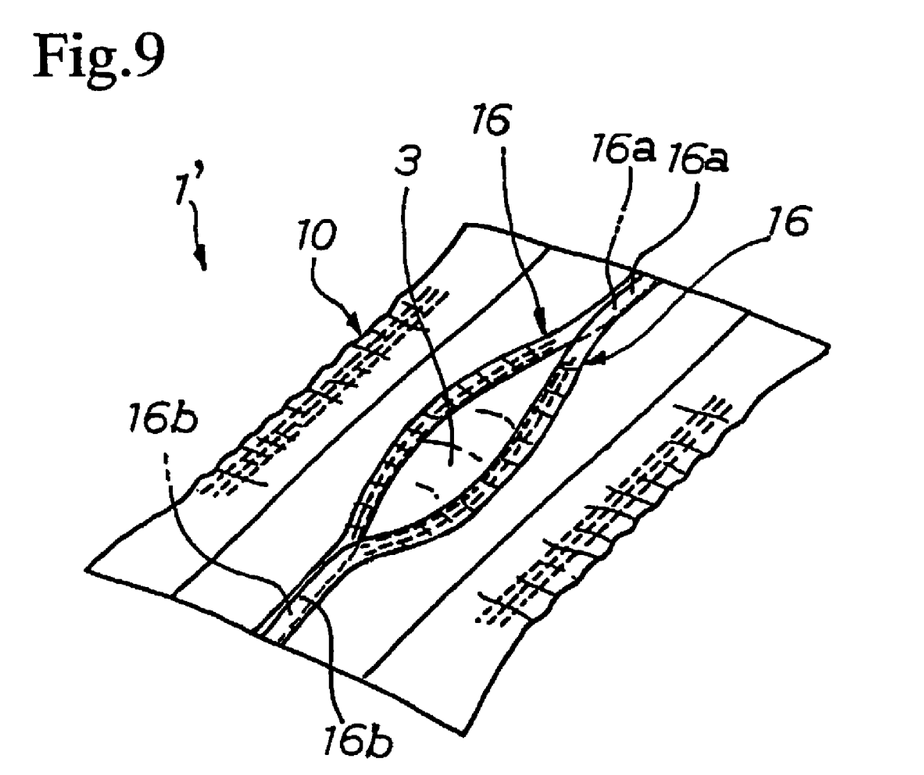
FIG. 9 is a schematic perspective view showing the backsheet side in a natural state of the urine absorbing pad shown in FIG. 7.

The two elastic expansible/contractible members 16 are, as shown in FIG. 9, overlapped with each other at the longitudinal end portions (end portions 16a, 16a and end portions 16b, 16b).

The length, width, etc. of the elastic expansible/contractible members 16 can be properly set. For example, the width of the elastic expansible/contractible member can be set to 0.05 to 20 cm, and the length (fixed length in the state shown in FIG. 7) of the portion (central portion), which is not fixed to the main body portion 10, of the elastic expansible/contractible members 16 can be set to 1.0 to 20 cm, and the ratio of the length with respect to the entire length of the main body portion 10 can be set to 0.05 to 0.95.

The urine absorbing pad 1' of this invention is put on the wearer in a state where the main body portion 10 is deformed in such a manner as to form a concavity on the topsheet 2 side and the deformed configuration is maintained by the two elastic expansible/contractible members 16, 16.

Figures 10A, 10B, 10C:
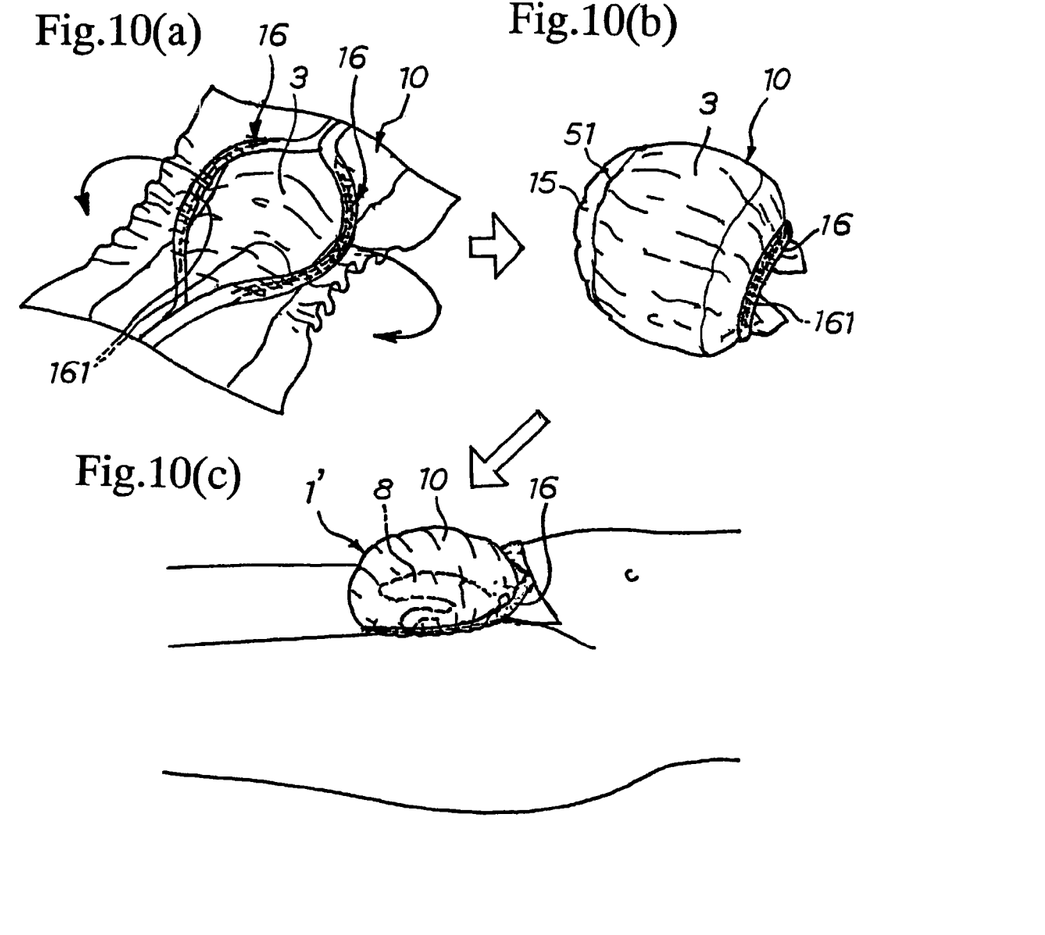
FIG. 10(a), FIG. 10(b) and FIG. 10(c) are explanatory views showing one example of a method for using the urine absorbing pad shown in FIG. 7.

FIGS. 10(a) through 10(c) are explanatory views when the pad 1' is put on in such a manner as to cover a male's liquid excretion portion (penis) (in case the pad 1' is used as a male urine absorbing pad).

First, as shown in FIG. 10(a), the two elastic expansible/contractible members 16, 16 are picked with the fingers and pulled leftwards and rightwards so as to form a space for pushing a part of the main body portion 10 therein between the elastic expansible/contractible members 16, 16. At the same time, the central portion of the main body portion 10 of the urine absorbing pad 1' is pushed from the topsheet 2 side with the finger so that the central portion is pressed into between the elastic expansible/contractible members 16, 16.

As shown in FIG. 10(b), after the topsheet 2 side of the pad 1' is greatly depressed so that the main body portion 10 is formed into a bowl-like configuration, the hand is separated from the elastic expansible/contractible members 16. In that state, since the periphery of the main body portion 10 which is deformed into a bowl-like configuration, is pushed by elastic expanding/contracting force of the elastic expansible/contractible members, the deformed configuration is stably maintained.

Then, as shown in FIG. 10(c), the deformed pad 1' is put on the male's liquid excretion portion (penis) 8. Such a deformed state is stably maintained during wearing.

According to the urine absorbing pad 1' of this embodiment, the pad 1' can easily be deformed into a configuration (for example, such a configuration as shown in FIG. 10(b) or 10(c)) suited for exhibiting absorptive performance and the deformed configuration is stably maintained during wearing.

Owing to the above features, excellent absorptive performance can be obtained and positional displacement of the pad 1' can be prevented during wearing. In addition, the pad 1' can be put on without manually directly touching the male's liquid excretion portion 8.

Moreover, in this embodiment, since the opposite end portions 16a, 16a of the elastic expansible/contractible members 16, 16 are fixed to the widthwise generally central portion of the main body portion 10, the central portion of the pad 1' or main body portion 10 pushed between the elastic expansible/contractible members is pressed by its peripheral entirety. Accordingly, a deeper concavity can be formed. Thus, the pad 1' is further enhanced in shape retainability of the deformed configuration during wearing. Particularly, since the longitudinal end portions of the two elastic expansible/contractible members 16 are overlapped with each other, such an effect as just mentioned is more significantly enhanced.

Also in the absorbent core 4 of this embodiment, as shown in FIG. 8, the boundary portions between the central absorbent core 41 and the opposite side absorbent cores 42 each function as a flexible axis 44. By providing the flexible axis 44 to the absorbent core 4, the degree of freedom of deformation of the absorbent core is increased and a deeper concavity can be formed on the topsheet 2 side. Thus, wearability for the wearer, absorptive performance, etc. can be further enhanced.

Moreover, the part of the absorbent core 4 which is overlapped with the flexible axis 44 or the those parts of the absorbent core 4 which are overlapped with the opposite side absorbent cores 42 are each preferably provided with an elastic member 9 along the flexible axis 44. In FIG. 8, although the elastic member 9 is disposed between the side absorbent core and the topsheet, it may be disposed between the side absorbent core and the backsheet or between the side absorbent core and the second backsheet 15.

Figure 11:
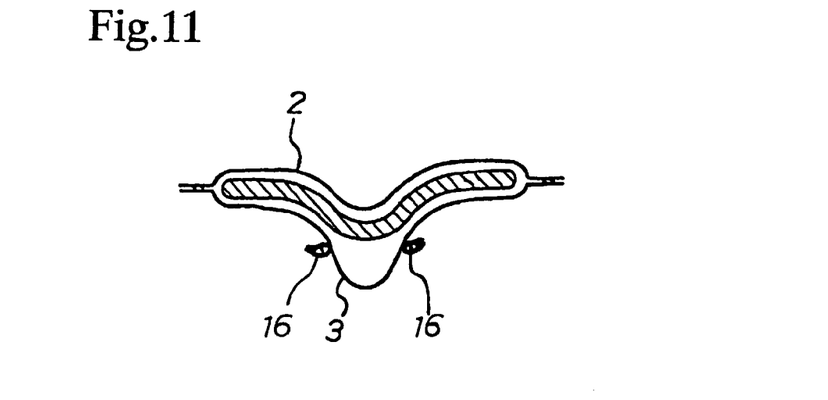
FIG. 11 is a view for explaining another method for using the urine absorbing pad shown in FIG. 7 and is a schematic sectional view showing a widthwise section of the urine absorbing pad in a state shown in FIG. 10(a)
Figure 12A:
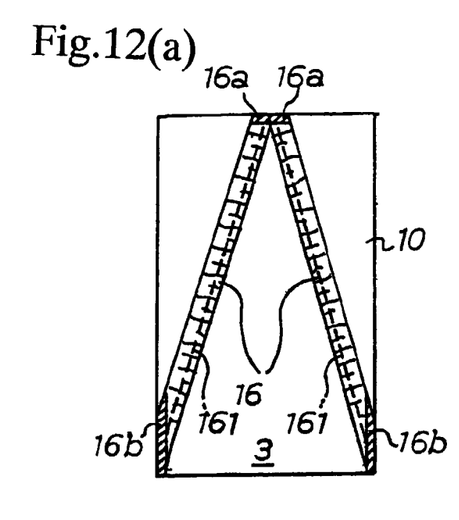
FIG. 12(a), FIG. 12(b), FIG. 12(c) and FIG. 12(d) are schematic plan views showing other embodiments of the present invention.
Figure 12B:
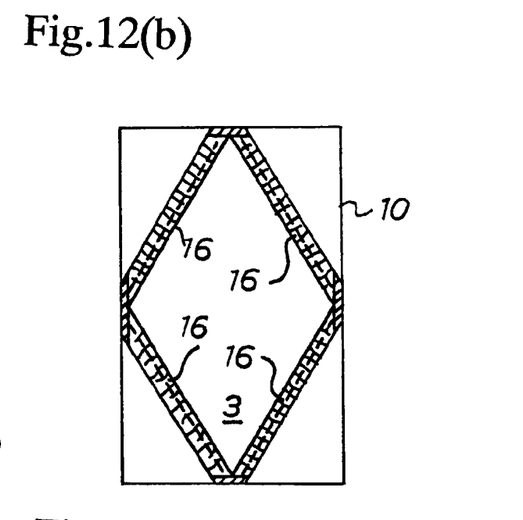
Figure 12C:
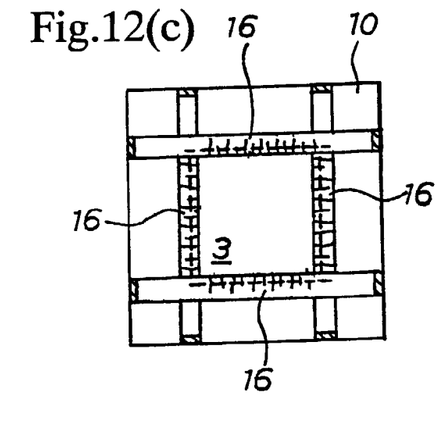
Figure 12D:
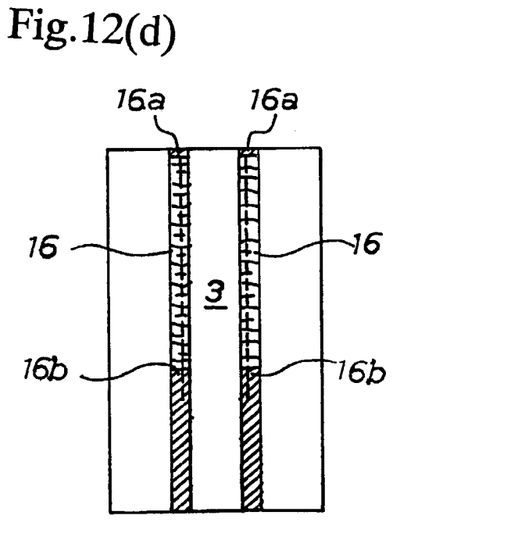

The urine absorbing pad 1' of this embodiment can also be used by fixing its configuration by the elastic expansible/contractible members 16 at the deformed stage of the main body portion shown in FIGS. 10(a) and 11. In that case, for example, the concavity on the topsheet 2 side is abutted with the male's or female's liquid excretion portion.

The material for forming the urine absorbing pad 1' of this embodiment will now be described. As for the material for forming the topsheet 2, the backsheet 3 and the absorbent core 4, the material conventionally used for forming an absorbent article of a sanitary napkin, a disposable diaper, etc. can be used without any particular limitation.

As a material for forming the second backsheet 15, the same liquid impermeable material as the backsheet 3 can be used.

As the belt-like sheet 162 for forming the elastic expansible/contractible members 16, a nonwoven fabric, a resin film, a woven fabric, a knitted fabric, a lamination thereof, and the like can be used. Among them, a nonwoven fabric, particularly, a hydrophilic nonwoven fabric is preferable. As for the material of the elastic member 161, a synthetic rubber, a natural rubber, a spandex and the like can be listed. As a form of the elastic member 161, a thread-like form, a belt-like form, a film-like form and the like can be listed. As the elastic members 7 and 9, the same material and form as in the case of the elastic member 161 can be used.

The fourth invention is not limited to the above-mentioned embodiment. Many changes and modifications can be made without departing from the gist of the invention.

For example, in the above-mentioned embodiment of the fourth invention, although the elastic expansible/contractible members 16 comprising the sheet material 162 and the elastic member 161 are used, an elastic expansible/contractible members, the entire or a part of which is formed of an elastic film can be used.

Moreover, the elastic expansible/contractible members 16 may be disposed and fixed in the manner as shown in FIGS. 12(a) through 12(d).

Moreover, the two elastic expansible/contractible members 16 may be connected at opposite end portions so as to form an annular configuration. In the above-mentioned embodiment, although a single surface of the absorbent core 4 is covered with three sheets, in total, of the backsheet 3 and the second backsheets 15, it may also be covered with only one backsheet having a large width.

The absorbent article of the fourth invention may be a sanitary napkin, a panty liner, a disposable diaper, etc. besides the urine absorbing pad (including an incontinent pad).

The absorbent article of the fourth invention can easily be deformed into a configuration suited for exhibiting absorptive performance and the configuration is stably maintained during wearing.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising
a liquid permeable topsheet,
a liquid impermeable backsheet,
a liquid retentive absorbent core interposed between said topsheet and said backsheet, and
two sheet-like members provided at a side edge portion thereof with an elastic member, each of said sheet-like members having an elongated configuration in the same direction as said absorbent article, each of said sheet-like members having a first side edge portion along the longitudinal direction on the sheet-like member, said first side edge portion being a free edge located in the lengthwise and widthwise center of said absorbent article and having said elastic member disposed thereon, and each of said sheet-like members having a second side edge portion along the longitudinal direction on the sheet-like member, said second side edge portion being a fixed edge fixed to a backsheet side of said absorbent article opposite to said first side edge portion, said two sheet like members being fixed to a backsheet side of said absorbent article at mutually opposing end edge portions,
wherein, in a planarly expanded state of the absorbent article, in a longitudinal central portion of the absorbent article, the sheet-like members are overlapped with one another at both first side edge portions of said two sheet-like members, and wherein said free edges of said first side edge portions where said elastic members are disposed constitute an opening between said sheet-like members,
wherein said sheet-like members and said topsheet form a concavity on a topsheet side of the absorbent article, and wherein said concavity is maintained when said absorbent article is put on a wearer.

2. An absorbent article comprising
a liquid permeable topsheet,
a liquid impermeable backsheet,
a liquid retentive absorbent core interposed between the topsheet and the backsheet, and
at least two sheet-like members, which are provided at a side edge portion thereof with an elastic member, each of said sheet-like members having an elongated configuration in the same direction as said absorbent article, each of said sheet-like members having a first side edge portion along the longitudinal direction on the sheet-like member, said fast side edge portion being a free edge located in the lengthwise and widthwise center of said absorbent article and having said elastic member disposed thereon, and each of said sheet-like members having a second side edge portion along the longitudinal direction on the sheet-like member, said second side edge portion being a fixed edge fixed to a backsheet side of said absorbent article opposite to said first side edge portion, said at least two sheet like members being fixed to a backsheet side of said absorbent article at mutually opposing end edge portions,
wherein said sheet-like members and said topsheet form on said topsheet side, and wherein said concavity is maintained when said absorbent article is put on a wearer and
wherein, in a planarly expanded state of the absorbent article, in a longitudinal central portion of the absorbent article, said two sheet-like members are overlapped with each other at each first side edge portion of said at least two sheet-like members, and wherein said free edges of said first side edge portions where said elastic members are disposed constitute an opening between said sheet-like members.

3. An absorbent article comprising
a liquid permeable topsheet,
a liquid retentive absorbent core,
on the opposite side of said topsheet with respect to said absorbent core, a liquid impermeable backsheet or a liquid impermeable backsheet and a side portion sheet, and
at least two sheet-like members, which are each provided at a side edge portion thereof with an elastic member, each of said sheet-like members having an elongated configuration in the same direction as said absorbent article, each of said sheet-like members having a first side edge portion along the longitudinal direction on the sheet-like member, said first side edge portion being a free edge located in the lengthwise and widthwise center of said absorbent article and having said elastic member disposed thereon, and each of said sheet-like members having a second side edge portion along the longitudinal direction on the sheet-like member, said second side edge portion being a fixed edge fixed to a backsheet side of said absorbent article opposite to said first side edge portion, said at least two sheet like members being fixed to a backsheet side of said absorbent article at mutually opposing end edge portions,
wherein, in a planarly expanded state of the absorbent article, in a longitudinal central portion of the absorbent article, the sheet-like members are overlapped with one another at each first side edge portion of said at least two sheet-like members, and wherein said free edges of said first side edge portions where said elastic members are disposed constitute an opening between said sheet-like members, and
wherein, before the use of said absorbent article, said side edge portion where said elastic member is disposed at each of said two sheet-like members is positioned on the backsheet side of said absorbent article.

* * * * *

UNITED STATES PATENT AND TRADEMARK OFFICE
CERTIFICATE OF CORRECTION

PATENT NO. : 7,651,487 B2
APPLICATION NO. : 10/345303
DATED : January 26, 2010
INVENTOR(S) : Niki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this

Twenty-third Day of November, 2010

David J. Kappos
*Director of the United States Patent and Trademark Office*